(12) United States Patent
Callahan et al.

(10) Patent No.: US 6,433,023 B1
(45) Date of Patent: Aug. 13, 2002

(54) COMPOSITIONS HAVING ANTI-LEISHMANIAL ACTIVITY

(75) Inventors: Heather Callahan, Lajolla, CA (US); Colleen Kelley, Flagstaff, AZ (US); Max Grogl, Columbia, MD (US); Brian G. Schuster, Vienna, VA (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 09/048,334

(22) Filed: Mar. 26, 1998

(Under 37 CFR 1.47)

Related U.S. Application Data

(60) Provisional application No. 60/042,267, filed on Mar. 31, 1997.

(51) Int. Cl.$^7$ .............................................. A61K 31/095
(52) U.S. Cl. ....................................... 514/706; 514/741
(58) Field of Search .................................. 514/706, 741

(56) References Cited

PUBLICATIONS

CA 124:306519, Callahan et al, Antimicrob. Agents Chemother. 40(4), 947–52, abstract, 1996.*

\* cited by examiner

*Primary Examiner*—Rebecca Cook
(74) *Attorney, Agent, or Firm*—Elizabeth Arwine

(57) ABSTRACT

This invention is directed to a composition comprising 4-chloro-3,6-dinitrobenzotrifluoride and related compounds and method for using it to treat infections caused by organisms that have microtubules.

15 Claims, No Drawings

COMPOSITIONS HAVING ANTI-LEISHMANIAL ACTIVITY

This application takes priority from Provisional Application No. 60/042,267, filed Mar. 31, 1997.

FIELD OF THE INVENTION

This invention relates to chloralin (4-chloro-3,5 dinitrobenzotrifluoride) and related compounds for use against parasites having microtubules, including Gardia, Plasmodium, Trypanosome and Leishmania parasites.

BACKGROUND OF THE INVENTION

Leishmaniasis is a disease that presents a major public health problem worldwide, with approximately 12 million to 40 million persons estimated to be infected. Previously the treatment of choice has been pentavalent antimony in the form of sodium stribogluconate or megluminic antimonate. Both agents are administered intravenously and produce severe adverse side effects. Hospitalization of the patient during treatment is required. Clinical failures are not uncommon. Drugs that are more easily administered and are less toxic are required.

Microtubule inhibitors have been exploited previously as antihelminthic drugs, in cancer therapy and as herbicides. Trifluralin, a microtubule inhibiting herbicide, has been shown to inhibit Leishmania species. The mechanism of action of these microtubule inhibitors in plants has been studied. Dinitroaniline herbicides such as oryzalin and trifluralin interact directly with the major microtubule protein, tubulin, leading to disruption of mitosis.

Although antimicrobial dinitroaniline herbicides show great potential as antiprotozoal compounds, disputed indications of potential carcinogenicity will probably keep trifluralin from being developed for human use.

DESCRIPTION OF THE INVENTION

It is the purpose of this invention to provide improved means for treating infections caused by organisms that have microtubules by administration of 4-chloro-3, 6-dinitrobenzotrifluoride and related compounds which may be administered at a dosage sufficient to attain a blood concentration of 0.5 $\mu$M to 500 $\mu$M.

Materials and Methods 3-chloro-3,5-dinitrobenzotrifluoride (compound 1), 4-chloro-3-nitrobenzotrifluoride (compound 4), 3-amino-4-chlorobenzotrifluoride (compound 5), 2-bromo-3,5(bis (trifluoromethyl)aniline (compound 6), 4-methoxy-3-nitrobenzotrifluoride (compound 7), and 2-nitro-4-(trifluoromethyl)thiophenol (compound 8) were obtained from Aldrich Chemical Company and were used to without further purification. Trifluralin was obtained from Reidel de Haen and was used without further purification. 4-chloro-3-nitro-5-sulfonylbenzotrifluoride (compound 2) and 4-chloro-3-nitro-5-carboxybenzotrifluoride (compound 3) were obtained from the Walter Reed Army Institute of Research inventory and were used without further purification. All of the agents were initially dissolved in dimethyl sulfoxide and were then diluted at 100 fold in parasitic culture medium before being tested against Leishmania species.

Of the seven compounds tested, the chloralin and compounds 2, 4, and 8 were found to be much more effective than trifluralin.

A comparison of the antiparasitic activities of analogues with electron withdrawing groups of different strengths but the same leaving group Cl, showed a correlation between the strength of the electron-withdrawing group and the activity of the compound against Leishmania promastigotes.

Compounds of the invention are of the formula:

Formula I

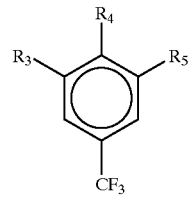

wherein $R_4$ is a leaving group such as chloro, alkoxy, bromo, an amino which forms a primary or secondary amine, hydroxy or thiol; $R_3$ and $R_5$ are H, nitro, amino, $CF_3$, carboxy or sulfonyl group, wherein at least one of $R_3$ and $R_5$ is nitro. The compounds, when tested, showed the following concentrations to be effective at the $IC_{50}$ level:

TABLE I

| | |
|---|---|
| Chloralin (4-chloro-3,5 dinitrobenzotrifluoride) | .89 $\mu$M |
| 4-chloro-3-nitro-5-sulfonylbenzotrifluoride | 6.1 $\mu$M |
| 4-chloro-3-nitro-5-carboxybenzotrifluoride | 120 $\mu$M |
| 4-chloro-3-nitrobenzotrifluoride | 35 $\mu$M |
| 3-amino-4-chlorobenzotrifluoride | 77 $\mu$M |
| 2-bromo-3,5-bis(trifluoromethyl)aniline | 26 $\mu$M |
| 4-methoxy-3-nitrobenzotrifluoride | 68 $\mu$M |
| 2-nitro-4-(trifluoromethyl)thiophenol | 15 $\mu$M |

Of particular value are the compounds wherein $R_4$ is chloro and $R_5$ and $R_3$ are nitro or a sulfur containing substituent such as sulfonyl.

The active agents may be administered systemically to attain the effective blood concentration of 0.5 $\mu$M to 500 $\mu$M concentration in the blood. For example, the active agents may be administered orally, intramuscularly or, in the case of a severely ill patient, intravenously, in appropriate pharmaceutical carrier. Additionally, for cutaneous infections, the active agents may, for example, be administered as salves, ointments, gels, or lotions to the affected areas. Furthermore, the compounds, when given with transdermal carriers, may be administered dermally for systemic effect.

Compositions for administration are exemplified. However, such examples should not be viewed as limiting the invention.

EXAMPLE 1

Composition for parenteral use or use as spray:

| | |
|---|---|
| 4-chloro-3,5 dinitro benzotrifluoride | 10 mg. |
| phosphate buffered saline | 5 ml. |

EXAMPLE 2

Composition for parenteral use:

| | |
|---|---|
| 4,chloro-3-nitro-5-sulfonylbenzotrifluoride | 10 mg. |
| 10% glucose in 1/2 normal saline | 10 ml |

EXAMPLE 3

Composition for topical use

| 2-nitro-4-(trifluoromethyl)thiophenol | 50 mg |
|---|---|
| propylene glycol | 5 ml |

EXAMPLE 4

For transdermal application, a patch composed of trilaminate of an adhesive matrix sandwiched between a non-permeable backing and a protective covering layer is prepared in the following manner:

To a pressure-sensitive silicone adhesive composition BIOPSA™ Q7-2920 (Dow Corning Corp., Midland, Mich., U.S.A.) in cyclohexane (50% w/v) is added sufficient amounts of Compound 2 to provide a composition containing 10% compound 2. The adhesive is applied to a polyester film to provide in successive layers to provide about 2 mg of active agent per cm². The film containing the adhesive is then made into patches of 10 cm². The patches would be covered with a protective layer to be removed before application of the patch. Patches may be prepared containing permeation enhancers such as cyclodextrin, butylated hydroxyanisole, or butylated hydroxytoluene.

EXAMPLE 5

The following composition is useful for oral administration:

| 2-nitro-4-(trifluoromethyl)thiophenol | 10 mg |
|---|---|
| starch | 495 mg |

The composition is placed in a capsule for oral administration

What we claim is:

1. A pharmaceutical composition of matter comprising an antiparasitic effective amount of a compound of the formula I

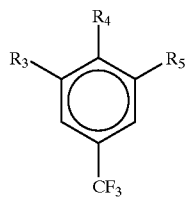

wherein $R_4$ is a leaving group selected from the group consisting of chloro, alkoxy, bromo, an amino which forms a primary or secondary amine, hydroxy and thiol; $R_3$ and $R_5$ are selected from the group consisting of H, nitro, amino, $CF_3$, carboxy and a sulfur containing group, wherein at least one of $R_3$ and $R_5$ is nitro, in a pharmaceutically acceptable carrier.

2. A composition of claim 1 wherein, in formula I, $R_4$ is Cl and one of $R_3$ and $R_5$ is nitro and the other of $R_3$ and $R_5$ is nitro or a sulfur-containing group.

3. A composition of claim 1 wherein $R_4$ is Cl and $R_3$ and $R_5$ are both nitro.

4. A composition of claim 2 wherein one of $R_3$ and $R_5$ is thiol.

5. A composition of claim 2 wherein one of $R_3$ and $R_5$ is sulfonyl.

6. A composition of claim 1 wherein $R_4$ is bromo.

7. A method of inhibiting growth of a parasite having microtubules in a person infected with said parasite comprising administration of an antiparasitic effective amount of the composition of claim 1.

8. A method of claim 7 wherein, in formula I, $R_4$ is Cl and one of $R_3$ and $R_5$ is nitro and the other of $R_3$ and $R_5$ is nitro or a sulfur-containing group.

9. A method of claim 8 wherein, in formula I, $R_4$ is Cl and $R_3$ and $R_5$ are both nitro.

10. A method of claim 8 wherein, in formula I, one of $R_3$ and $R_5$ is thiol.

11. A method of claim 8 wherein, in formula I, one of $R_3$ and $R_5$ is sulfonyl.

12. A method of claim 7 wherein the composition is administered parenterally.

13. A method of claim 7 wherein the composition is administered orally.

14. A method of claim 7 wherein the composition is administered topically.

15. A method of claim 7 wherein the composition is administered transdermally.

* * * * *